United States Patent
Watkins et al.

(10) Patent No.: US 8,017,342 B2
(45) Date of Patent: Sep. 13, 2011

(54) SOLID PHASE IMMOBILIZATION OF PHOSPHOLIPIDS AND COFACTOR PROTEINS VIA COVALENT ATTACHMENT

(75) Inventors: Michael Watkins, Vacaville, CA (US); Tony Prestigiacomo, San Francisco, CA (US); Steven Binder, Berkeley, CA (US); Woei Tan, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 1046 days.

(21) Appl. No.: 11/406,674

(22) Filed: Apr. 18, 2006

(65) Prior Publication Data

US 2006/0234392 A1 Oct. 19, 2006

Related U.S. Application Data

(60) Provisional application No. 60/672,745, filed on Apr. 18, 2005.

(51) Int. Cl.
*G01N 33/53* (2006.01)
(52) U.S. Cl. ............... 435/7.1; 435/7.2; 436/518
(58) Field of Classification Search ............ 530/339, 530/340, 345, 395, 400; 436/71, 87
See application file for complete search history.

(56) References Cited

U.S. PATENT DOCUMENTS

| | | | |
|---|---|---|---|
| 4,193,983 A * | 3/1980 | Ullman et al. | 436/528 |
| 5,162,505 A * | 11/1992 | Dean et al. | 530/391.5 |
| 5,344,758 A | 9/1994 | Krilis et al. | |
| 5,506,110 A | 4/1996 | Matsuura et al. | |
| 5,998,223 A | 12/1999 | Matsuura et al. | |
| 6,777,193 B1 | 8/2004 | Baeza-Ramirez et al. | |
| 7,169,892 B2 * | 1/2007 | Atsushi et al. | 530/328 |
| 2004/0096903 A1 | 5/2004 | Lang et al. | |

FOREIGN PATENT DOCUMENTS

| | | |
|---|---|---|
| CA | 2072548 A1 | 12/1993 |
| WO | WO 91/10138 A1 | 7/1991 |
| WO | WO 97/40387 | 10/1997 |
| WO | WO 99/64595 | 12/1999 |
| WO | WO 02/066990 A2 | 8/2002 |

OTHER PUBLICATIONS

Horkko, S., et al. The epitopes for some antiphospholipid antibodies are adducts of oxidized phospholipid and beta-2 glycoprotein 1 (and other proteins). Proc. Natl. Acad. Sci. USA. 1997;94:10356-10361.*
Niedermann, G., et al. Carboxyacyl derivatives of cardiolipin as four-tailed hydrophobic anchors for the covalent coupling of hydrophilic proteins to liposomes. Biochim. Biophys. Acta. 1991;1070:401-408.*
Ishimori et al. (J. Immunological Methods 1984, vol. 75, p. 351-360).*
Thermo Scientific Instruction year 2008.*
Chamley, L.W., et al.; "Cofactor Dependent and Cofactor Independent Anticardiolipin Antibodies;" *Thrombosis Research*; 1991; vol. 61; pp. 291-299.

(Continued)

*Primary Examiner* — Jacob Cheu
(74) *Attorney, Agent, or Firm* — Kilpatrick Townsend & Stockton LLP

(57) ABSTRACT

The present invention provides methods and reagents for detecting anti-phospholipid-cofactor protein-antibodies.

16 Claims, 4 Drawing Sheets

OTHER PUBLICATIONS

Giles, Ian P., et al.; "How Do Antiphospholipid Antibodies Bind $\beta_2$-Glycoprotein I?;" *Arthritis & Rheumatism*; Aug. 2003; vol. 48; No. 8; pp. 2111-2121.

Guglielmone, H., et al.; "Cofactor Dependence and Isotype Distribution of Anticardiolipin Antibodies in Viral Infections;" 2001; *Ann Rheum Dis*; vol. 60; pp. 500-504.

Harris, E. Nigel and Khamashta, Munther; "Anticardiolipin Test and the Antiphospholipid (Hughes) Syndrome: 20 Years and Counting;" *The Journal of Rheumatology*; 2004; vol. 31; No. 11; pp. 2099-2101.

Levine, Jerrold S., M.D., et al.; "The Antiphospholipid Syndrome;" *N Engl J Med*, Mar. 7, 2002; vol. 346; No. 10; pp. 752-763.

Nimmo, Michael C., M.D., et al.; "The Antiphospholipid Antibody Syndrome A Riddle Wrapped in a Mystery Inside an Enigma;" 2003; *Clinical and Applied Immunology Reviews*; vol. 4; pp. 125-140.

Passam, Freda H. and Krillis, Steven, A.; "Laboratory Tests for the Antiphospholipid Syndrome: Current Concepts;" *Pathology*; Apr. 2004; vol. 36; No. 2; pp. 129-138.

Wilson, Wendell A., et al.; "International Consensus Statement on Preliminary Classification Criteria for Definite Antiphospholipid Syndrome;" *Arthritis & Rheumatism*; Jul. 1999; vol. 42; No. 7; pp. 1309-1311.

\* cited by examiner

FIGURE 1
A.
| | | |
|---|---|---|
| ◯ | = | carrier (*e.g.*, microparticle, microtiter plate) |
| P | = | phospholipid (*e.g.*, cardiolipin, phosphatidylethanolamine or phosphatidylserine) |
| ∼ | = | linker (*e.g.*, 1,6 diaminohexane, bovine serum albumin – BSA) |
| ✬ | = | phospholipid co-factor protein (*e.g.*, prothrombin, β2GPI) |
B. 
C. 
D. 

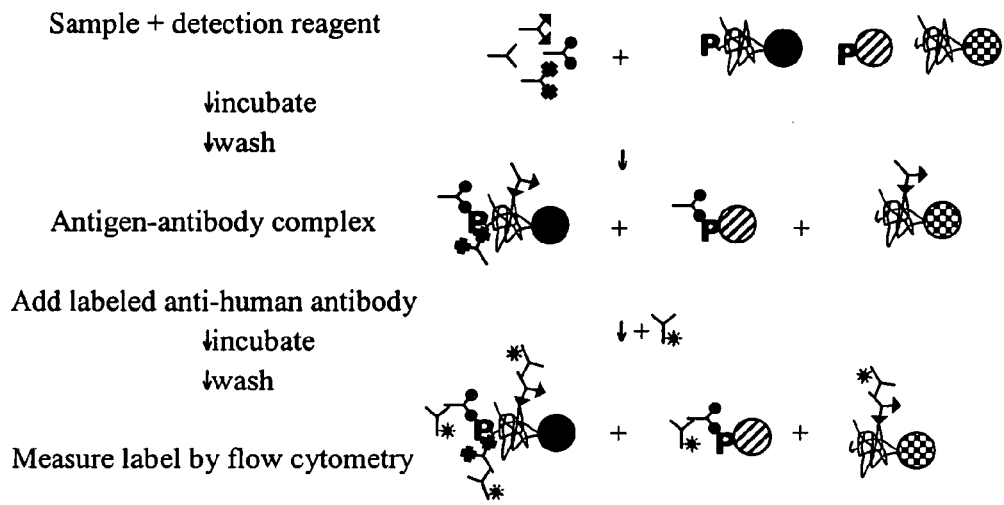

Sample + detection reagent
↓incubate
↓wash

Antigen-antibody complex

Add labeled anti-human antibody
↓incubate
↓wash

Measure label by flow cytometry

B.

| | |
|---|---|
| ● ◐ ⊛ | = differentiable microparticles |
| ⊣ | = non-specific human IgG (in sample) |
| ⊣ | = cofactor specific antibodies (in sample) |
| ⊣ | = phospholipid specific antibodies (in sample) |
| ⊣ | = antibody specific for the phospholipid-cofactor complex (in sample) |
| ⊁ | = labeled anti-human IgG antibody |
| P | = phospholipid |
| ∿ | = linker |
| ⊛ | = phospholipid co-factor protein |

SOLID PHASE IMMOBILIZATION OF PHOSPHOLIPIDS AND COFACTOR PROTEINS VIA COVALENT ATTACHMENT

CROSS-REFERENCES TO RELATED APPLICATIONS

This application claims the benefit of U.S. Provisional Application No. 60/672,745, filed Apr. 18, 2005, which is herein incorporated by reference for all purposes.

BACKGROUND OF THE INVENTION

Antiphospholipid syndrome (APS), first described in 1983, is now recognized as a major thrombotic syndrome with clinical features that range from deep vein thrombosis (DVT), chronic leg ulcers, recurrent miscarriages, headache, heart attacks, renal vein and artery thrombosis, to pulmonary embolism and even pulmonary hypertension, associated with antiphospholipid antibodies (e.g., cardiolipin). Phospholipids are lipids or fats that are insoluble in hydrophilic environments. Current immunoassay technology uses hydrophobic attractions to bind phospholipids to the hydrophobic surface of a microtiter plate. The conventional enzyme-linked immunosorbent assay (ELISA) for anti-cardiolipin antibodies uses cardiolipin that is passively coated on a solid phase, onto which various cofactor proteins are adsorbed. The configuration of this format is able to detect, but is not efficient in differentiating, a heterogeneous group of anti-cardiolipin antibodies that include cofactor-dependent and independent antibodies against cardiolipin. Moreover, the passive configuration is difficult to reproducibly manufacture and is not stable in an aqueous environment. The detection of these anti-cardiolipin antibodies is influenced by the amount and quality of bovine serum and the subsequent fluctuation of the level of cofactor proteins added to the assay. In addition, the passive configuration of the cofactor protein-phospholipid complexes will not withstand the presence of detergents such as Tween20 and CHAPS, which are commonly added to the assay to reduce non-specific binding and to enhance sensitivity and specificity. Detergents interfere in anti-phospholipid immunoassays by solubilizing the lipid bound to the solid phase and thereby causing a loss in signal (see WO91100138, US2004096903). Thus, users have frequently reported variability in assays for anti-cardiolipin antibodies. The present invention solves this and other needs.

BRIEF SUMMARY OF THE INVENTION

In one aspect, the present invention provides an anti-phospholipid-cofactor protein-antibody detection reagent that comprises a phospholipid moiety, a cofactor protein, and a carrier. The phospholipid moiety is covalently bound to the cofactor protein and the cofactor protein is bound to the carrier. The phospholipid moiety can be, e.g., a cardiolipin moiety, a phosphatidylserine moiety, a phosphatidylcholine moiety, a phosphatidylethanolamine moiety, a phosphatidylglycerol moiety, a phophatidylinositol moiety, or a phosphatidic acid moiety. Examples of cofactor proteins include the beta-2-glycoprotein I (β2GPI) protein and the prothrombin protein. Examples of carriers include a microparticle and a microtiter plate. In one embodiment, the cofactor protein is covalently bound to the carrier.

In another aspect, the invention provides a method of detecting an anti-phospholipid-cofactor protein-antibody in a biological sample by contacting the biological sample with the anti-phospholipid-cofactor protein-antibody detection reagent described above and detecting an antigen-antibody complex comprising the anti-phospholipid-cofactor protein-antibody detection reagent and the anti-phospholipid-cofactor protein-antibody. Detection of the antigen-antibody complex indicates the presence of the anti-phospholipid-cofactor protein-antibody in the biological sample. The antibody specifically binds to e.g., a phospholipid moiety, a cofactor protein, or a phospholipid-cofactor protein complex. As above, examples of carriers include a microparticle and a microtiter plate. In one embodiment, detection is performed by flow cytometry. In another embodiment, at least one step, e.g., an incubation or washing step is performed in a buffer that comprises a detergent.

In another aspect, the anti-phospholipid-cofactor protein-antibody detection reagent described above is used to diagnose anti-phospholipid syndrome (APS) in a patient, by obtaining a biological sample from the patient, contacting the biological sample with the anti-phospholipid-cofactor protein-antibody detection reagent, and determining the level of an antigen-antibody complex comprising the anti-phospholipid-cofactor protein-antibody detection reagent and an anti-phospholipid-cofactor protein-antibody in the biological sample. The level of the antigen antibody complex is compared to a normal control and a difference in the level of the antigen-antibody complex in the biological sample as compared to the normal control indicates that the patient has APS. In one embodiment, the level of antigen antibody complex in a patient diagnosed with APS is higher than the level of the normal control. Examples of carriers include a microparticle and a microtiter plate. In a preferred embodiment, the biological sample is blood or a blood product. In another preferred embodiment, detection is performed using flow cytometry. In a further embodiment, the phospholipid is cardiolipin or phosphatidylserine and the cofactor protein is beta-2-glycoprotein I (β2GPI). In another embodiment, the method includes an additional step of determining a level of an antibody that binds to a phosphatidylserine-β2GPI protein complex, wherein the a phosphatidylserine-β2GPI protein complex comprises a phosphatidylserine moiety covalently bound to the β2GPI protein and comparing that to a level of the antibody from a normal control.

In another aspect, the invention provides a method of determining a likelihood of developing anti-phospholipid syndrome (APS) in a patient, by first determining a level of an antibody that binds to an antigen for APS, e.g., a cardiolipin moiety, a beta-2-glycoprotein I (β2GPI) protein, or a complex of cardiolipin covalently bound to the β2GPI protein. The levels of antibodies from the patient are compared with levels of the antibodies from a normal control. Patients with levels of the antibody that are less than or substantially equal to levels of the antibody from the normal control indicate have low or no likelihood of developing APS. Patients with levels of the antibody that are higher than levels of the antibody from the normal control have an increased likelihood of developing APS. In one embodiment, a level of an antibody that binds to a phosphatidylserine-β2GPI protein complex is determined and compared to a level from a normal control. In a further embodiment, the phosphatidylserine moiety is covalently bound to the β2GPI protein.

In another aspect, the invention provides a method of detecting an family of antibodies to phospholipids, cofactor proteins and phospholipid-cofactor proteins in a biological sample. The detected antibodies specifically bind to the antigens selected from the group consisting of a cardiolipin moiety, a beta-2-glycoprotein I (β2GPI) protein, and a cardiolipin-β2GPI protein complex, a phosphatidylserine moiety, a phosphatidylserine-β2GPI protein complex and a prothrombin protein. Any one of the antibodies or any combination of the antibodies can be detected in this method. The method is performed by contacting the biological sample with differentiable paramagnetic latex particles coated with either a cardiolipin moiety, a beta-2-glycoprotein I (β2GPI) protein, a cardiolipin-β2GPI protein complex, a phosphatidylserine-β2GPI protein complex or a prothrombin protein, and then detecting an antigen-antibody complex bound to this reagent. The detection of the antigen-antibody complex indicates that antibodies are present in the biological sample. In one embodiment the carrier is differentiable paramagnetic latex particles. In another embodiment, detection and differentiation is performed by flow cytometry.

In one aspect, the present invention provides an anti-cardiolipin-cofactor protein-antibody detection reagent, which includes a cardiolipin moiety, a beta-2-glycoprotein I (β2GPI) protein, and a carrier. The cardiolipin moiety is covalently bound to the β2GPI protein and the β2GPI protein is bound to the carrier. In one embodiment, the β2GPI protein is covalently bound to the carrier. In some embodiments the carrier can be, e.g., a microsphere or a microtiter plate.

In another aspect, the invention provides a method of detecting an anti-cardiolipin-cofactor protein-antibody in a biological sample. The detected antibody specifically binds to an antigen selected from the group consisting of a cardiolipin moiety, a beta-2-glycoprotein I (β2GPI) protein, and a cardiolipin-β2GPI protein complex. The method is performed by contacting the biological sample with the anti-cardiolipin-cofactor protein-antibody detection reagent described above, and then detecting an antigen-antibody complex comprising the anti-cardiolipin-cofactor protein-antibody detection reagent and the anti-cardiolipin-cofactor protein-antibody. The detection of the antigen-antibody complex indicates that the anti-cardiolipin-cofactor protein-antibody is present in the biological sample. In some embodiments the carrier can be, e.g., a microparticle or a microtiter plate. In another embodiment, detection is performed by flow cytometry.

In yet another aspect, the invention provides a method of diagnosing anti-phospholipid syndrome (APS) in a patient. First, a biological sample is isolated from the patient. The biological sample is then contacted with the anti-cardiolipin-cofactor protein-antibody detection reagent described above. Then, a level of an antigen-antibody complex comprising the anti-cardiolipin-cofactor protein-antibody detection reagent and an anti-cardiolipin-cofactor protein-antibody from the biological sample is determined. The detection of the antigen-antibody complex indicates that the anti-cardiolipin-cofactor protein-antibody is present in the biological sample. The patient level of anti-cardiolipin-cofactor protein-antibody is compared to the level of a normal control and difference in levels between the patient and the normal control indicates that the patient has APS. A difference in levels between the patient and the normal control can also indicate that the patient has a symptom of APS. In some embodiments, the carrier can be, e.g., a microparticle or a microtiter plate. In another embodiment, detection is performed by flow cytometry. In yet another embodiment, the biological sample is blood or a blood product.

BRIEF DESCRIPTION OF THE DRAWINGS

FIGS. 1A-D show the structures of phospholipid cofactor protein detection reagents. FIG. 1A provides the symbols used for reagent components. FIG. 1B provides the structures of reagents that detect antibodies that bind to phospholipid-cofactor proteins. FIG. 1C provides the structures of reagents that detect antibodies that bind to phospholipid moieties. FIG. 1D provides the structures of reagents that detect antibodies that bind to phospholipid-cofactor protein complexes.

FIG. 2 provides a schematic of a flow cytometric assay used to distinguish between antibodies that bind to a phospholipid moiety, a cofactor protein, and a phospholipid-cofactor protein complex. FIG. 2A depicts the assay and FIG. 2B provides the symbols used for assay components.

DETAILED DESCRIPTION OF THE INVENTION

I. Introduction

Figure 3:
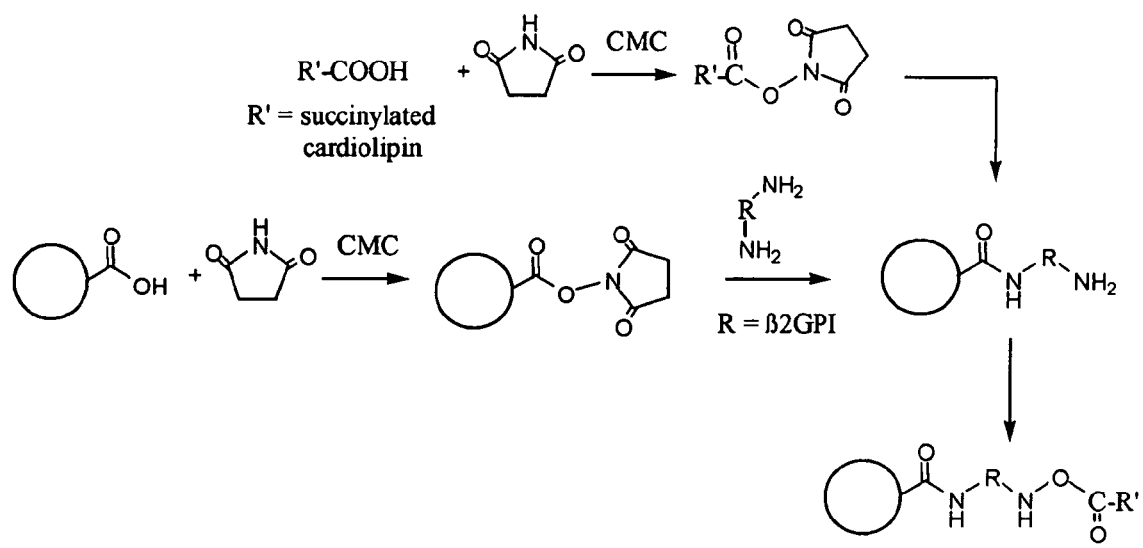
FIG. 3 provides a schematic for synthesis of a cardiolipin-β2GPI microparticle. The microparticle is depicted as a large circle. CMC refers to N-cyclohexyl-N'-(2-morpholinoethyl)carbodiimide metho-p-toluenesulfonate. β2GPI refers to the beta-2-glycoprotein I (β2GPI) protein.

The present invention relates to reagents and methods to detect so called anti-cardiolipin antibodies in a biological sample. The reagents are beads or other solid support that include, for the first time, cardiolipin covalently bound to the beta-2-glycoprotein I (β2GPI) protein. The β2GPI protein, in turn, is bound to a solid support or carrier to facilitate use of the reagent in immunoassays.

The present invention also relates to methods to use the reagents to detect anti-cardiolipin-cofactor protein-antibodies, and to methods to diagnose anti-phospholipid syndrome (APS) using the reagents.

II. Definitions

As used herein "an anti-phospholipid-cofactor protein-antibody" refers to an antibody that specifically binds to a phospholipid moiety, a phospholipid cofactor protein, or a complex of a phospholipid moiety and a phospholipid cofactor protein. In one embodiment, the anti-phospholipid-cofactor protein-antibody specifically binds to a cardiolipin moiety, a beta-2-glycoprotein I (β2GPI) protein, or a complex of a cardiolipin moiety and a β2GPI protein or other cofactor protein. In another embodiment, the anti-phospholipid-cofactor protein-antibody specifically binds to a phosphatidylserine moiety, a beta-2-glycoprotein I (β2GPI) protein, or a complex of a phosphatidylserine moiety and a β2GPI protein or other cofactor protein.

As used herein "an anti-phospholipid-cofactor protein-antibody detection reagent" refers to a detection reagent that comprises a phospholipid moiety, that is covalently bound to a phospholipid cofactor protein, which in turn, is bound to a carrier. In one embodiment, the anti-phospholipid-cofactor protein-antibody detection reagent comprises a cardiolipin moiety, that is covalently bound to a β2GPI protein, which in turn, is bound to a carrier. In another embodiment, the cardiolipin moiety includes a succinyl group to facilitate the covalent binding to the β2GPI protein or other cofactor protein. In yet another embodiment, the anti-phospholipid-cofactor protein-antibody detection reagent comprises a phosphatidylserine moiety, that is covalently bound to a β2GPI protein, which in turn, is bound to a carrier. In another embodiment, the phosphatidylserine moiety includes a succinyl group to facilitate the covalent binding to the β2GPI protein or other cofactor protein.

As used herein "an anti-phospholipid antibody" refers to an antibody that specifically binds to a phospholipid moiety in a biological sample in the absence of added cofactor protein.

As used herein "an anti-phospholipid antibody detection reagent" refers to a detection reagent that comprises a phospholipid moiety that is covalently bound to a carrier. In preferred embodiments, the phospholipid moiety includes a succinyl group to facilitate the covalent binding to the carrier.

As used herein, "a phospholipid moiety" refers to, e.g., cardiolipin, phosphatidylserine, phosphatidylcholine, phosphatidylethanolamine, phosphatidylglycerol, phophatidylinositol, and phosphatidic acid. Phospholipids are well known and are commercially available from, e.g., Avanti Polar Lipids, Inc. and Sigma-Aldrich Co. A phospholipid moiety encompasses acyl group of all lengths and amounts of saturation. A phospholipid moiety also encompasses a phospholipid that has been modified to include a reactive carboxyl group. In one preferred embodiment, a succinyl group is included in the phospholipid moiety.

As used herein, "a phospholipid cofactor protein" is a protein that specifically binds to a phospholipid moiety. Examples of phospholipid cofactor proteins include, e.g., the β2GPI protein and prothrombin.

As used herein "an anti-cardiolipin-cofactor protein-antibody" refers to an antibody that specifically binds to a cardiolipin moiety, a cardiolipin cofactor protein, or a complex of a cardiolipin moiety and a cardiolipin cofactor protein. In one embodiment, the anti-cardiolipin-cofactor protein-antibody specifically binds to a cardiolipin moiety, a beta-2-glycoprotein I (β2GPI) protein, or a complex of a cardiolipin moiety and a β2GPI protein.

As used herein "an anti-cardiolipin-cofactor protein-antibody detection reagent" refers to a detection reagent that comprises a cardiolipin moiety, that is covalently bound to a cardiolipin cofactor protein, β2GPI protein, which in turn, is bound to a carrier. In one embodiment, the anti-cardiolipin-cofactor protein-antibody detection reagent comprises a cardiolipin moiety, that is covalently bound to a β2GPI protein, which in turn, is bound to a carrier. In another embodiment, the cardiolipin moiety includes a succinyl group to facilitate the covalent binding to the β2GPI protein or other cofactor protein.

As used herein "an anti-cardiolipin antibody" refers to an antibody that specifically binds to a cardiolipin moiety in a biological sample in the absence of added β2GPI protein.

As used herein "an anti-cardiolipin antibody detection reagent" refers to a detection reagent that comprises a cardiolipin moiety that is covalently bound to a carrier. In preferred embodiments, the cardiolipin moiety includes a succinyl group to facilitate the covalent binding to the carrier.

As used herein, "a cardiolipin moiety" refers to the phospholipid cardiolipin. Cardiolipin is well known and is commercially available from, e.g., Avanti Polar Lipids, Inc. and Sigma-Aldrich Co. Cardiolipin has four acyl groups and a cardiolipin moiety encompasses acyl group of all lengths and amounts of saturation. Cardiolipin moiety also encompasses cardiolipin that has been modified to include a reactive carboxyl group. In a preferred embodiment, a succinyl group is included in the cardiolipin moiety. In a further preferred embodiment, the succinyl modification takes place on the C2 position of the cardiolipin polar head group.

As used herein, "a cardiolipin cofactor protein" is a protein that specifically binds to cardiolipin. In a preferred embodiment, a cardiolipin cofactor protein is a β2GPI protein.

As used herein "an anti-phosphatidylserine-cofactor protein-antibody" refers to an antibody that specifically binds to a phosphatidylserine moiety, a phosphatidylserine cofactor protein, or a complex of a phosphatidylserine moiety and a phosphatidylserine cofactor protein. In one embodiment, the anti-phosphatidylserine-cofactor protein-antibody specifically binds to a phosphatidylserine moiety, a beta-2-glycoprotein I (β2GPI) protein, or a complex of a phosphatidylserine moiety and a β2GPI protein. In another embodiment, the anti-phosphatidylserine-cofactor protein-antibody specifically binds to a phosphatidylserine moiety, a prothrombin protein, or a complex of a phosphatidylserine moiety and a prothrombin protein.

phosphatidylcholine, phosphatidylethanolamine, phosphatidylglycerol, phophatidylinositol, and phosphatidic acid The invention also encompasses other anti-phospholipid-cofactor protein-antibodies, including e.g., anti-phosphatidylcholine-cofactor protein-antibody, anti-phosphatidylethanolamine-cofactor protein-antibody, anti-phosphatidylglycerol-cofactor protein-antibody, anti-phophatidylinositol-cofactor protein-antibody, and anti-phosphatidic acid-cofactor protein-antibody.

As used herein "an anti-phosphatidylserine-cofactor protein-antibody detection reagent" refers to a detection reagent that comprises a phosphatidylserine moiety, that is covalently bound to a phosphatidylserine cofactor protein, which in turn, is bound to a carrier. In one embodiment, the anti-phosphatidylserine-cofactor protein-antibody detection reagent comprises a phosphatidylserine moiety, that is covalently bound to a β2GPI protein or a prothrombin protein, which in turn, is bound to a carrier. In another embodiment, the phosphatidylserine moiety includes a succinyl group to facilitate the covalent binding to the cofactor protein.

The invention also encompasses other an anti-phospholipid-cofactor protein-antibody detection reagents, including e.g., anti-phosphatidylcholine-cofactor protein-antibody detection reagent, anti-phosphatidylethanolamine-cofactor protein-antibody detection reagent, anti-phosphatidylglycerol-cofactor protein-antibody detection reagent, anti-phophatidylinositol-cofactor protein-antibody detection reagent, and anti-phosphatidic acid-cofactor protein-antibody detection reagent.

As used herein "an anti-phosphatidylserine antibody" refers to an antibody that specifically binds to a phosphatidylserine moiety in a biological sample in the absence of added β2GPI protein.

The invention also encompasses other anti-phospholipid antibodies, including e.g., anti-phosphatidylcholine antibody, anti-phosphatidylethanolamine antibody, anti-phosphatidylglycerol antibody, anti-phophatidylinositol antibody, and anti-phosphatidic acid antibody.

As used herein "an anti-phosphatidylserine antibody detection reagent" refers to a detection reagent that comprises a phosphatidylserine moiety that is covalently bound to a carrier. In preferred embodiments, the phosphatidylserine moiety includes a succinyl group to facilitate the covalent binding to the carrier.

The invention also encompasses other anti-phospholipid antibody detection reagents, including e.g., anti-phosphatidylcholine antibody detection reagent, anti-phosphatidylethanolamine antibody detection reagent, anti-phosphatidylglycerol antibody detection reagent, anti-phophatidylinositol antibody detection reagent, and anti-phosphatidic acid antibody detection reagent.

As used herein, "a phosphatidylserine moiety" refers to the phospholipid phosphatidylserine. Phosphatidylserine is well known and is commercially available from, e.g., Avanti Polar Lipids, Inc. and Sigma-Aldrich Co. A phosphatidylserine moiety encompasses acyl group of all lengths and amounts of saturation. A phosphatidylserine moiety also encompasses phosphatidylserine that has been modified to include a reactive carboxyl group. In a preferred embodiment, a succinyl group is included in the phosphatidylserine moiety.

The invention also encompasses other phospholipid moieties, including e.g., a phosphatidylcholine moiety, a phosphatidylethanolamine moiety, a phosphatidylglycerol moiety, a phophatidylinositol moiety, and a phosphatidic acid moiety.

As used herein, "a phosphatidylserine cofactor protein" is a protein that specifically binds to phosphatidylserine. In a preferred embodiment, a phosphatidylserine cofactor protein is a β2GPI protein or a prothrombin protein.

The invention also encompasses other phospholipid cofactor proteins, including e.g., a phosphatidylcholine cofactor protein, a phosphatidylethanolamine cofactor protein, a phosphatidylglycerol cofactor protein, a phophatidylinositol cofactor protein, and a phosphatidic acid cofactor protein.

As used herein, "beta-2-glycoprotein I" or "β2GPI", also known as apolipoprotein H, is a plasma protein that binds to anionic surfaces, including cardiolipin. In a preferred embodiment, β2GPI is derived from a human source. Human β2GPI is known, Accession number P02749, and is commercially available from, e.g., Haematologic Technologies, Inc.

As used herein, "prothrombin" or "prothrombin protein" refers to a plasma protein that is converted into thrombin during blood clotting. In a preferred embodiment, prothrombin is derived from a human source. An amino acid sequence for prothrombin is found, e.g., at Accession number NP_000497 and is commercially available from, e.g., Haematologic Technologies, Inc.

As used herein, "carrier" refers to an inert solid support of natural material, such as glass and collagen, or synthetic material, such as acrylamide, cellulose, nitrocellulose, silicone rubber, polystyrene, polyethylene vinyl acetate, polypropylene, polymethacrylate, polyethylene, polysilicates, polyethylene oxide, polycarbonates, teflon, fluorocarbons, nylon, polyanhydrides, polyglycolic acid, polylactic acid, polyorthoesters, polypropylfumarate, glycosaminoglycans, and polyamino acids. Frequently, some functional groups, e.g., carboxylic acid (—COOH), free amine (—NH$_2$), and sulfhydryl (—SH) groups, naturally present on the surface of a carrier can be used for linkage to, e.g., a cardiolipin moiety or a protein, such as β2GPI. In case no such functional group is naturally available, a desired functional group, such as a carboxylic acid group, or a moiety known to be a partner of a binding interaction (such as avidin that is capable of binding biotin) may be attached to such solid support. Preferred carriers of the present invention are e.g., an ELISA plate, a microtiter plate, or a carboxylated latex or magnetic microsphere or microparticle.

As used herein, "a normal control" refers to a biological sample of e.g., blood, serum, or plasma, that is representative of the range of anti-cardiolipin cofactor protein antibody levels in healthy individuals, i.e., individuals who do not have APS. A normal control can also be a reference range of anti-cardiolipin-cofactor protein-antibody, i.e., a range of anti-cardiolipin-cofactor protein-antibody levels determined in individuals who do not have APS.

"Specific detection" as used herein refers to the fact that detection of any antibody bound to the anti-cardiolipin-cofactor protein antibody detection reagents of the present invention is determinative of the presence of an anti-cardiolipin-cofactor protein antibody, often in a heterogeneous population of other antibodies and proteins. Under designated immunoassay conditions, a detectable signal is designated as one that is at least twice the background signal. Thus, specific antibody-peptide binding should yield a signal at least two times, preferably more than 10 times, and more preferably more than 100 times the background.

The term "biological sample" refers to sections of tissues such as biopsy and autopsy samples, and frozen sections taken for histological purposes. Such samples may include whole blood, serum, plasma, cerebrospinal fluid, sputum, tissue, cultured cells, e.g., primary cultures, explants, transformed cells, stool, urine, vesicle fluid, mucus, and other bodily secretion, or tissue that could be sampled with a swab device. In preferred embodiments, a biological sample is blood or a blood product, e.g., whole blood, serum, dried blood spot, or plasma. A biological sample is typically obtained from a human who has or is suspected to have APS.

The term "contact" or "contacting" is used herein interchangeably with the following: combined with, added to, mixed with, passed over, incubated with, flowed over, etc.

The term "antibody" denotes a protein of the immunoglobulin family or a polypeptide including fragments of an immunoglobulin that is capable of noncovalently, reversibly, and in a specific manner binding a corresponding antigen. An illustrative antibody structural unit includes a tetramer. Each tetramer is composed of two identical pairs of polypeptide chains, each pair having one "light" (about 25 kD) and one "heavy" chain (about 50-70 kD), connected through one or more disulfide bonds. The recognized immunoglobulin genes include the κ, λ, α, γ, δ, ε, and μ constant region genes, as well as the myriad immunoglobulin variable region genes. Light chains are classified as either κ or λ. Heavy chains are classified as γ, μ, α, δ, or ε, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain ($V_L$) and variable heavy chain ($V_H$) refer to these regions of light and heavy chains respectively. Anti-cardiolipin-cofactor protein antibodies or anti-cardiolipin antibodies can be from any immunoglobin class.

The term "complementarity-determining domains" or "CDRs" refers to the hypervariable regions of $V_L$ and $V_H$. The CDR is the target protein-binding site of the antibody chain that harbors specificity for that target protein. There are three CDRs (CDR1-3, numbered sequentially from the N-terminus) in each human $V_L$ or $V_H$, constituting about 15-20% of the variable domains. The CDRs are structurally complementary to the epitope of the target protein and are thus directly responsible for the binding specificity. The remaining stretches of the $V_L$ or $V_H$, the so-called framework regions, exhibit less variation in amino acid sequence (Kuby, *Immunology*, 4th ed., Chapter 4, W.H. Freeman & Co., New York, 2000).

The positions of the CDRs and framework regions are determined using various well known definitions in the art, e.g., Kabat, Chothia, International ImMunoGeneTics database (IMGT), and AbM (see, e.g., Johnson et al., *Nucleic Acids Res.*, 29:205-206 (2001); Chothia and Lesk, *J. Mol. Biol.*, 196:901-917 (1987); Chothia et al., *Nature*, 342:877-883 (1989); Chothia et al., *J. Mol. Biol.*, 227:799-817 (1992); Al-Lazikani et al., *J. Mol. Biol.*, 273:927-748 (1997)). Definitions of antigen combining sites are also described in the following: Ruiz et al., *Nucleic Acids Res.*, 28:219-221 (2000); and Lefranc, M. P., *Nucleic Acids Res.*, 29:207-209 (2001); MacCallum et al., *J. Mol. Biol.*, 262:732-745 (1996); and Martin et al, *Proc. Natl. Acad. Sci. USA*, 86:9268-9272 (1989); Martin et al., *Methods Enzymol.*, 203:121-153 (1991); and Rees et al., In Sternberg M. J. E. (ed.), *Protein Structure Prediction*, Oxford University Press, Oxford, 141-172 (1996).

The terms "antibody light chain" and "antibody heavy chain" denote the $V_L$ or $V_H$, respectively. The $V_L$ is encoded by the gene segments V (variable) and J (junctional), and the $V_H$ is encoded by V, D (diversity), and J. Each of $V_L$ or $V_H$ includes the CDRs as well as the framework regions.

Antibodies exist as intact immunoglobulins or as a number of well-characterized fragments produced by digestion with various peptidases. Thus, for example, pepsin digests an antibody below the disulfide linkages in the hinge region to produce $F_{(ab)}'_2$, a dimer of $F_{ab}'$ which itself is a light chain joined to $V_H$-$C_H$1 by a disulfide bond. The $F_{(ab)}'_2$ may be reduced under mild conditions to break the disulfide linkage in the hinge region, thereby converting the $F_{(ab)}'_2$ dimer into an $F_{ab}'$ monomer. The $F_{ab}'$ monomer is essentially $F_{ab}$ with part of the hinge region (Paul, *Fundamental Immunology* 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain $F_v$) or those identified using phage display libraries (see, e.g., McCafferty et al., *Nature*, 348:552-554 (1990))

For preparation of monoclonal or polyclonal antibodies, any technique known in the art can be used (see, e.g., Kohler & Milstein, *Nature*, 256:495-497 (1975); Kozbor et al., *Immunology Today*, 4:72 (1983); Cole et al., *Monoclonal Antibodies and Cancer Therapy*, pp. 77-96. Alan R. Liss, Inc. 1985). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies, and heteromeric $F_{ab}$ fragments, or scFv fragments that specifically bind to selected antigens (see, e.g., McCafferty et al., supra; Marks et al., *Biotechnology*, 10:779-783, (1992)).

III. Attachment of a Phospholipid to a Cofactor Protein and/or to a Carrier

Phospholipids can be attached to a cofactor protein and/or to a carrier for use in the detection reagents of the present invention. Many phospholipids naturally include a reactive group and can be conjugated to a functional group on another molecule using conventional methods. In some embodiments, phospholipids with naturally occurring reactive groups are modified to provide a second reactive group.

Unlike many other phospholipids, cardiolipin does not naturally contain a reactive group such as a carboxyl group. Thus, cardiolipin must be modified to provide a reactive group for attachment to a cofactor protein, such as β2GPI protein, or to a carrier. In one embodiment, cardiolipin is derivatized with succinic anhydride to yield succinylated-cardiolipin. Succinylation of cardiolipin is known. See, e.g., published U.S. Patent Application 2004/0096903 and WO91/10138. In a preferred embodiment, the modification takes place on the C2 position of the cardiolipin polar head group.

After addition of a reactive group, the modified cardiolipin is conjugated to a functional group on another molecule. These reactions are conventional and are known in the art. For example, modified cardiolipin can be conjugated directly to a carrier. Carriers are described in more detail below. Frequently, a carrier has some functional groups, such as amine, carboxylic acid, and sulfhydryl groups, with which the functional groups of a modified cardiolipin molecule may easily react and establish a covalent bond that conjugates the cardiolipin and the carrier. In case there is no functional group naturally present on a carrier suitable for this purpose, the carrier may be derivatized to expose or to attach additional reactive functional groups prior to conjugation. The derivatization may involve attachment of any of a number of molecules such as those available from Sigma-Aldrich Chemical Company, St. Louis, Miss. Examples include 1,6 diaminohexane, BSA, poly-lysine, Poly(ethylene glycol) bis(3-aminopropyl) terminated, Poly(ethylene oxide), four-arm, amine terminated and aminodextran from Invitrogen Corporation, Carlsbad, Calif.

The modified cardiolipin can also be conjugated to a cofactor protein, such as β2GPI protein. The cofactor protein, e.g., β2GPI protein, is then bound to a carrier, either by noncovalent binding; or by a covalent bond between the carrier and a terminal amino acid residue of the cofactor protein, or between the carrier and an internal amino acid residue of the cofactor protein. If necessary the carrier will be derivatized to expose or to attach an appropriate additional reactive functional groups prior to conjugation to the cofactor protein. These reactions are conventional and are known in the art. FIG. 2 provides a schematic of a modified cardiolipin covalently bound to a β2GPI protein, which in turn is covalently bound to a carrier, i.e., a bead. The cofactor protein, e.g., β2GPI protein can be bound to the carrier before or after attachment of the modified cardiolipin to the cofactor protein. In a preferred embodiment, succinylated cardiolipin conjugated to a β2GPI protein. In another preferred embodiment, the β2GPI protein is covalently bound to a carrier.

Similar methods can be used to attach other phospholipids to a protein or to a carrier. Other phospholipids include phosphatidyserine, phosphatidylcholine, phosphatidylethanolamine, phosphatidylglycerol, phophatidylinositol, and phosphatidic acid. Some of these phospholipids do contain reactive groups they can be conjugated to a protein or a carrier in an unmodified state. However, if required or desired by the user, reactive groups as described above, e.g., a succinyl group, can be added to a phospholipid before conjugation.

A carrier is often a synthetic polymeric material, but may also be naturally-occurring. Examples of carrier material are acrylamide, cellulose, nitrocellulose, glass, polystyrene, polyethylene vinyl acetate, polypropylene, polymethacrylate, polyethylene, polysilicates, polyethylene oxide, polycarbonates, teflon, fluorocarbons, nylon, silicon rubber, collagen, polyanhydrides, polyglycolic acid, polylactic acid, polyorthoesters, polypropylfumarate, glycosaminoglycans, and polyamino acids. A carrier may be in one of the many useful forms including thin films or membranes, beads, bottles, dishes, fibers, woven fibers, shaped polymers, particles, and microparticles such as microspheres. Preferred forms of supports are plates and beads. The most preferred form of beads is magnetic beads or latex beads.

Covalent binding of cofactor protein, e.g., β2GPI protein, to a carrier is described above. Cofactor proteins can also be non-covalently bound to a carrier. In some embodiments, a cofactor protein or cofactor protein covalently bound to cardiolipin is coated on wells of a microtiter plate and then allowed to attach to the surface, thereby non-covalently binding the cofactor protein to the microtiter well. In a further embodiment, a β2GPI protein or β2GPI protein covalently bound to cardiolipin is coated on wells of a microtiter plate and then allowed to attach to the surface, thereby non-covalently binding the β2GPI protein to the microtiter well.

Alternatively, a cofactor protein such as β2GPI can be linked to a carrier via the known interaction of a tag and a tag-binder. One of the partners of this binding interaction, e.g., a tag, can be attached to the cofactor protein, e.g., recombinantly, whereas the other partner, e.g., a tag binder, can be attached to the carrier. A number of tags and tag binders can be used, based upon known molecular interactions well described in the literature. For example, where a tag has a natural binder, e.g., biotin, it can be used in conjunction with appropriate tag binders (avidin, streptavidin, neutravidin, etc.) Receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors. In addition, some synthetic polymers, such as polyurethanes, polyesters, polycarbonates, polyureas, polyamides, polyethyleneimines, polyarylene sulfides, polysiloxanes, polyimides, and polyacetates can form an appropriate tag or tag binder as well.

A tag can be attached to a cofactor protein via a number of ways. On the other hand, a tag binder can be fixed to a solid substrate (i.e., a carrier) using any of a variety of methods currently available. Solid substrates are commonly derivatized or functionalized by exposing all or a portion of the substrate to a chemical reagent which fixes a chemical group to the surface, and the chemical group is in turn reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:6031-6040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Examples of detection reagents are shown in FIG. 1. FIG. 1B shows a detection reagent comprising a cofactor protein bound to a carrier. The cofactor protein can be attached to the carrier through covalent or non-covalent bonds. The cofactor protein can be attached to a linker, which is then attached to the carrier, if desired by the user.

FIG. 1C shows a detection reagent comprising phospholipid bound to a carrier. The phospholipid can be covalently attached to a linker, which is then covalently or non-covalently attached to the carrier, if desired by the user.

FIG. 1D shows a detection reagent comprising a complex of a phospholipid and cofactor protein bound to a carrier. The cofactor protein can be attached to the carrier through covalent or non-covalent bonds. The phospholipid can be attached to a linker, which is then attached to the cofactor protein, if desired by the user. Similarly, the cofactor protein can be attached to a linker, which is then attached to the carrier, if desired by the user.

V. Assays for Anti-Phospholipid-Cofactor Protein Antibody or Anti-Phospholipid Antibody Detection A. Detection of Anti-Phospholipid-Cofactor Protein Antibodies Using Detection Reagents of the Present Invention In order for the detection reagents of the present invention to be useful for detection of anti-phospholipid-cofactor protein antibodies, they must first be able to bind anti-phospholipid-cofactor protein antibodies with specificity. To test such specific binding, a number of well known immunological binding assays can be performed. See, e.g., U.S. Pat. Nos. 4,366,241; 4,376,110; 4,517,288; and 4,837,168. For a general review of immunoassay methods, see also Asai, *Methods in Cell Biology*, Volume 37: *Antibodies in Cell Biology*, Academic Press, Inc. NY (1993).

Typically, the detection reagents of the present invention can be immobilized to a carrier and used as a so-called "capture agent" for anti-phospholipid-cofactor protein antibodies. Samples that are known to contain anti-phospholipid-cofactor protein antibodies may be used in binding assays to screen for cofactor proteins, including recombinant proteins such as recombinant β2GPI protein, that can bind anti-phospholipid-cofactor protein antibodies with specificity. Determination of proper binding conditions is well known and general instructions on performing such binding assays may be found in many scientific publications. See, e.g., Harlow and Lane, *Antibodies: A Laboratory Manual*, Cold Spring Harbor Laboratory (1988). Upon formation of the antibody-antigen (i.e., the detection reagent) complex, a labeling agent is used to indicate the presence of such complex. In the present case, there are several ways of using a labeling agent for this purpose. For instance, the labeling agent may be a second antibody that can recognize an antibody-antigen complex and bears a label. Alternatively, the second antibody may itself lack a label, but can in turn be bound by a labeled third antibody specific to antibodies of the species from which the second antibody is derived. The second antibody may also be modified with a detectable moiety, such as biotin, to which a third labeled molecule can bind with specificity, such as streptavidin with a label. In addition, other proteins capable of specifically binding immunoglobulin constant regions, such as protein A or protein G, can also be used as labeling agents. These proteins are normal constituents of streptococcal bacteria cell walls, and exhibit a strong non-immunogenic reactivity toward immunoglobulin constant regions from a variety of species. See, generally, Kronval et al., *J. Immunol.,* 111: 1401-1406 (1973); and Akerstrom et al., *J. Immunol.,* 135: 2589-2592 (1985). If anti-cardiolipin-cofactor protein antibodies are being assayed in a human patient, so called anti-human antibodies can be used to detect the anti-cardiolipin-cofactor protein antibodies.

Throughout the assays, incubation and/or washing steps may be required after each combination of reagents. Incubation steps can vary from about 5 seconds to several hours, preferably from about 5 minutes to about 24 hours. The incubation time will vary, depending upon the assay format, particular peptides, volume of solution, concentrations, and the like. The assays are frequently carried out at ambient temperature, although they can be conducted over a range of temperatures, such as from about 10° C. to about 40° C.

In preferred embodiments, the buffers used in the incubation and/or wash steps include a detergent, e.g., Tween 20, CHAPS, NP-40, or other detergent commonly used in immunoassays.

Different means of labeling can be used for detection of antibody-antigen complex. A labeling moiety can be, e.g., a fluorescent molecule (such as fluorescein, rhodamine, Texas Red, and phycoerythrin) or an enzyme molecule (such as horseradish peroxidase, alkaline phosphatase, and β-galactosidase) attached to a second or a third antibody, allowing detection based on fluorescence emission or a product of a chemical reaction catalyzed by the enzyme. Radioactive labels involving various isotopes, such as $^3$H, $^{125}$I, $^{35}$S, $^{14}$C, or $^{32}$P, can also be attached to appropriate molecules, and detection of antibody-peptide complex can thus be made by any suitable methods that registers radioactivity, such as autoradiography. See, e.g., Tijssen, *"Practice and Theory of Enzyme Immunoassays," Laboratory Techniques in Biochemistry and Molecular Biology*, Burdon and van Knippenberg Eds., Elsevier (1985), pp. 9-20. An introduction to labels, labeling procedures, and detection of labels can also be found in Polak and Van Noorden, *Introduction to Immunocytochemistry*, 2d Ed., Springer Verlag, N.Y. (1997); and in Haugland, *Handbook of Fluorescent Probes and Research Chemicals*, a combined handbook and catalogue published by Molecular Probes, Inc. (1996).

B. Flow Cytometry

Flow cytometry is one of the preferred methods for detecting the presence of anti-phospholipid-cofactor protein antibodies, where the conjugated cofactor-protein, e.g., β2GPI protein, of the present invention are conjugated to suitable particles and specific binding of anti-phospholipid-cofactor protein antibodies is detected through the binding of a third molecule labeled with, e.g., fluorescence. Methods of and instrumentation for flow cytometry are known in the art, and can be used in the practice of the present invention. Flow cytometry in general resides in the passage of a suspension of the microparticles as a stream past a laser beam and the detection of fluorescent emission from each particle by a photo multiplier tube. Detailed descriptions of instrumentation and methods for flow cytometry are found in the literature. Examples are McHugh, "Flow Microsphere Immunoassay for the Quantitative and Simultaneous Detection of Multiple Soluble Analytes," *Methods in Cell Biology* 42, Part B (Academic Press, 1994); McHugh et al., "Microsphere-Based Fluorescence Immunoassays Using Flow Cytometry Instrumentation," *Clinical Flow Cytometry*, Bauer, K. D., et al., eds. (Baltimore, Md., USA: Williams and Williams, 1993), pp. 535-544; Lindmo et al., "Immunometric Assay Using Mixtures of Two Particle Types of Different Affinity," *J. Immunol. Meth.* 126: 183-189 (1990); McHugh, "Flow Cytometry and the Application of Microsphere-Based Fluorescence Immunoassays," *Immunochemica* 5: 116 (1991); Horan et al., "*Fluid Phase Particle Fluorescence Analysis*: Rheumatoid Factor Specificity Evaluated by Laser Flow Cytophotometry," *Immunoassays in the Clinical Laboratory*, 185-189 (Liss 1979); Wilson et al., "A New Microsphere-Based Immunofluorescence Assay Using Flow Cytometry," *J. Immunol. Meth.* 107: 225-230 (1988); Fulwyler et al., "Flow Microsphere Immunoassay for the Quantitative and Simultaneous Detection of Multiple Soluble Analytes," *Meth. Cell Biol.* 33: 613-629 (1990); Coulter Electronics Inc., United Kingdom Patent No. 1,561,042 (published Feb. 13, 1980); and Steinkamp et al., *Review of Scientific Instruments* 44(9): 1301-1310 (1973). Flow cytometry assays are also disclosed in U.S. Pat. Nos. 6,280,618 and 6,872,578; both of which are herein incorporated by reference.

The particles used in the practice of this invention are preferably microscopic in size and formed of a polymeric material. Polymers that will be useful as microparticles are those that are chemically inert relative to the components of the biological sample and to the assay reagents other than the binding member coatings that are affixed to the microparticle surface. Suitable microparticle materials will also have minimal autofluorescence, will be solid and insoluble in the sample and in any buffers, solvents, carriers, diluents, or suspending agents used in the assay, and will be capable of affixing to the appropriate coating material, preferably through covalent bonding. Examples of suitable polymers are polyesters, polyethers, polyolefins, polyalkylene oxides, polyamides, polyurethanes, polysaccharides, celluloses, and polyisoprenes. Crosslinking is useful in many polymers for imparting structural integrity and rigidity to the microparticle. The size range of the microparticles can vary and particular size ranges are not critical to the invention. In most cases, the microparticles will range in diameter from about 0.5 micrometers to about 100 micrometers, and preferably from about 0.3 micrometers to about 40 micrometers.

To facilitate the particle recovery and washing steps of the assay, the particles preferably contain a magnetically responsive material, i.e., any material that responds to a magnetic field. Separation of the solid and liquid phases, either after incubation or after a washing step, is then achieved by imposing a magnetic field on the reaction vessel in which the suspension is incubated, causing the particles to adhere to the wall of the vessel and thereby permitting the liquid to be removed by decantation or aspiration. Magnetically responsive materials of interest in this invention include paramagnetic materials, ferromagnetic materials, ferrimagnetic materials, and metamagnetic materials. Paramagnetic materials are preferred. Examples are iron, nickel, and cobalt, as well as metal oxides such as $Fe_3O_4$, $BaFe_{12}O_{19}$, CoO, NiO, $Mn_2O_3$, $Cr_2O_3$, and CoMnP.

The magnetically responsive material can be dispersed throughout the polymer, applied as a coating on the polymer surface or as one of two or more coatings on the surface, or incorporated or affixed in any other manner that secures the material in to the particle. The quantity of magnetically responsive material in the particle is not critical and can vary over a wide range. The quantity can affect the density of the microparticle, however, and both the quantity and the particle size can affect the ease of maintaining the microparticle in suspension for purposes of achieving maximal contact between the liquid and solid phase and for facilitating flow cytometry. An excessive quantity of magnetically responsive material in the microparticles may produce autofluorescence at a level high enough to interfere with the assay results. It is therefore preferred that the concentration of magnetically responsive material be low enough to minimize any autofluorescence emanating from the material. With these considerations in mind, the magnetically responsive material in a particle in accordance with this invention preferably ranges from about 0.05% to about 75% by weight of the particle as a whole. A more preferred weight percent range is from about 1% to about 50%, a still more preferred weight percent range is from about 2% to about 25%, and an even more preferred weight percent range is from about 2% to about 8%.

Coating of the particle surface with the appropriate assay reagent can be achieved by electrostatic attraction, specific affinity interaction, hydrophobic interaction, or covalent bonding. Covalent bonding is preferred. The polymer can be derivatized with functional groups for covalent attachment of the assay reagent by conventional means, notably by the use of monomers that contain the functional groups, such monomers serving either as the sole monomer or as a co-monomer. Examples of suitable functional groups are amine groups (—$NH_2$), ammonium groups (—$NH_3^+$ or —$NR_3^+$), hydroxyl groups (—OH), carboxylic acid groups (—COOH), and isocyanate groups (—NCO). Useful monomers for introducing carboxylic acid groups into polyolefins, for example, are acrylic acid and methacrylic acid.

Linkers can be used as a means of increasing the density of antibody-recognizable epitopes on the particle surface and decreasing steric hindrance. This will increase the range and sensitivity of the assay. Linkers can also be used as a means of adding specific types of reactive groups to the solid phase surface if needed to secure the particular coating materials of this invention. Examples of suitable useful functional groups are 1,6 diaminohexane, polylysine, polyaspartic acid, polyglutamic acid, and polyarginine.

In some embodiments, care should be taken to avoid the use of particles that exhibit high autofluorescence. Particles formed by conventional emulsion polymerization techniques from a wide variety of starting monomers are generally suitable since they exhibit at most a low level of autofluorescence. Conversely, particles that have been modified to increase their porosity and hence their surface area, i.e., those particles that are referred to in the literature as "macroporous" particles, are less desirable since they tend to exhibit high autofluorescence. A further consideration is that autofluorescence increases with increasing size and increasing percentage of divinylbenzene monomer.

The labels used in the labeled binding members may be any label that is capable of emitting detectable signal. Preferred such labels are fluorophores. A vast array of fluorophores are reported in the literature and thus known to those skilled in the art, and many are readily available from commercial suppliers to the biotechnology industry. Literature sources for fluorophores include Cardullo et al., *Proc. Natl. Acad. Sci. USA* 85: 8790-8794 (1988); Dexter, D. L., *J. of Chemical Physics* 21: 836-850 (1953); Hochstrasser et al., *Biophysical Chemistry* 45: 133-141 (1992); Selvin, P., *Methods in Enzymology* 246: 300-334 (1995); Steinberg, I. *Ann. Rev. Biochem.*, 40: 83-114 (1971); Stryer, L. *Ann. Rev. Biochem.*, 47: 819-846 (1978); Wang et al., *Tetrahedron Letters* 31: 6493-6496 (1990); Wang et al., *Anal. Chem.* 67: 1197-1203 (1995).

The following is a list of examples of fluorophores: BODIPY; coumarin; cyanine dyes; fluorescein; fluorescein isothiocyanate; Phycobiliproteins (B-phycoerythrin, R-phycoerythrin, etc); quantum dots; rhodamine B; rhodamine 123; rhodamine X isothiocyanate; sulforhodamine B; sulforhodamine 101; sulfonyl chloride derivative of sulforhodamine 101 (Texas Red); N,N,N',N'-tetramethyl-6-carboxyrhodamine (TAMRA); tetramethyl rhodamine; and tetramethyl rhodamine isothiocyanate (TRITC).

The attachment of any of these fluorophores to the binding molecules described above to form assay reagents for use in the practice of this invention is achieved by conventional covalent bonding, using appropriate functional groups on the fluorophores and on the binding members. The recognition of such groups and the reactions to form the linkages will be readily apparent to those skilled in the art.

Similarly, methods of and instrumentation for applying and removing a magnetic field as part of an automated assay are known to those skilled in the art and reported in the literature. Examples of literature reports are Forrest et al., U.S. Pat. No. 4,141,687 (Technicon Instruments Corporation, Feb. 27, 1979); Ithakissios, U.S. Pat. No. 4,115,534 (Minnesota Mining and Manufacturing Company, Sep. 19, 1978); Vlieger, A. M., et al., *Analytical Biochemistry* 205:1-7 (1992); Dudley, *Journal of Clinical Immunoassay* 14:77-82 (1991); and Smart, *Journal of Clinical Immunoassay* 15:246-251 (1992). All of the citations in this and the preceding paragraphs are incorporated herein by reference.

An example of a flow cytometric assay is provided in FIG. 2A. In this example more than one detection reagent is used to analyze a sample from a patient. The detection reagents are e.g., an anti-phospholipid-cofactor protein antibody detection agent, an anti-phospholipid antibody detection reagent, and an anti-cofactor protein detection reagent. The detection reagents include microparticles, and in this instance each microparticle can be distinguished from the other. Flow cytometry can be used to distinguish microparticles by, e.g., particle size. Other methods of distinguishing particles include (Tripatzos I., EP0126450): fluorescent or colored dyes, size. In another embodiment, the microparticles are not distinguishable, but are used individually to assay the sample from a patient. For example, the sample could be aliquotted into three separate tubes that contain three different detection reagents.

After the sample is added to the detection reagent(s), the mixture is incubated to allow binding of the appropriate antibody to an appropriate detection reagent and formation of an antigen-antibody complex. The complexes are washed to remove unbound non-specific antibodies. A labeled antibody that is specific for the antibody of the assay, i.e., an anti-human antibody for a sample from a human patient, is added to the antigen antibody complex and incubated for a time sufficient to allow specific binding of the labeled antibody to occur. The complexes are washed again to remove unbound labeled antibody. The amount of label in the sample is measured using flow cytometry.

VI. Diagnosis of Anti-Phospholipid Syndrome

Anti-phospholipid syndrome (APS) is a disease associated with, e.g., stroke, deep vein thrombosis, recurrent pregnancy loss, livedo, seizures, chorea, renal and liver vein thrombosis, thrombocytopenia, and pulmonary hypertension.

One method of diagnosing is measurement of so-called anti-phospholipid antibodies of a patient suspected to have APS. Currently available methods of measuring those so-called anti-phospholipid antibodies are highly variable and the present invention provides improvements on those methods by, e.g., providing detection reagents that include covalently bound phospholipids, such as covalently bound cardiolipin. Other methods include measuring levels of anti-phosphatidylserine antibodies or antibodies against a phosphatidylserine-cofactor protein complex. The phosphatidylserine-cofactor protein complex preferably includes the $\beta$2GPI protein.

APS is diagnosed by determining a level of anti-cardiolipin-cofactor protein antibodies in a biological sample from a patient suspected to have APS. Other antibodies that can be measured for diagnosis include, e.g., anti-cardiolipin antibodies, anti-phosphatidylserine, anti-ethanolamine antibodies, and anti-cofactor protein antibodies, such as anti-$\beta$2GPI protein and anti-prothrombin antibodies, and anti-phosphatidylserine-cofactor protein complex antibodies. The determination is done by contacting the biological sample with a detection reagent of the invention, e.g., an anti-cardiolipin-cofactor protein-antibody detection reagent of the invention, and determining a level of an antigen-antibody complex comprising, e.g., the anti-cardiolipin-cofactor protein-antibody detection reagent and an anti-cardiolipin-cofactor protein-antibody from the biological sample. Thus, the level of the antigen-antibody complex, i.e., the complex comprising the anti-cardiolipin-cofactor protein-antibody detection reagent and an anti-cardiolipin-cofactor protein-antibody, correlates with the amount of the anti-cardiolipin-cofactor protein antibody in the sample.

In a preferred embodiment, diagnosis is made by determining the level of anti-cardiolipin-cofactor protein antibodies that bind specifically to an anti-cardiolipin-cofactor protein-antibody detection reagent that comprises a cardiolipin moiety covalently bound to a $\beta$2GPI protein, which is bound to a carrier. In a further preferred embodiment, the β2GPI protein is covalently bound to a carrier.

The level of anti-cardiolipin-cofactor protein antibody or other antibody of interest in the patient's sample is preferably compared to a normal control. A normal control refers to a biological sample of e.g., human blood, serum, or plasma, that is representative of the range of anti-cardiolipin cofactor protein antibody levels in healthy individuals, i.e., individuals who do not have APS. A normal control can also be a reference range of anti-cardiolipin-cofactor protein-antibody, i.e., a range of anti-cardiolipin-cofactor protein-antibody levels determined in individuals who do not have APS. A diagnosis of APS is supported if the level of anti-cardiolipin-cofactor protein antibody is designated as significantly above a normal control level, e.g., at least two times, or in some embodiments more than 10 times, or in other embodiments more than 100 times the normal control. Determination of a normal control value is known in the art and is disclosed in e.g., Sasse E. A., *Reference Intervals and Clinical Decision Limits*, in Clinical Chemistry: Theory, Analysis and Correlation 365-398 (Lawrence A. Kaplan et al. eds., 3rd ed. 1996).

Detection of anti-cardiolipin-cofactor protein antibodies can be done using conventional immunoassay formats, e.g., ELISA or flow cytometry.

In a preferred embodiment, the patient is a human. In a further preferred embodiment, the patient has a high level of an antibody detected by a reagent described herein and also has at least one other symptom of APS. Other symptoms of APS include vascular thrombosis, pregnancy morbidity, and the presence of lupus anticoagulant in plasma. See, e.g., Wilson et al., *Arthr. & Rheum.* 422:1309-1311 (1999).

It must be noted that as used herein and in the appended claims, the singular forms "a", "and", and "the" include plural referents unless the context clearly dictates otherwise. Thus, for example, reference to "a nucleic acid" includes a plurality of such nucleic acids and reference to "the polypeptide" includes reference to one or more polypeptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. Citations are incorporated herein by reference.

EXAMPLES

Example 1

Synthesis of Cardiolipin-β2GPI Protein-Beads

Into a 1.8 mL microfuge tube we placed 10 mg of 8 μm carboxylate-modified paramagnetic microspheres. We washed once (using magnetic separation) with about 1 mL of 167 mM MES at a pH of about 6.1. We added about 300 μL of 668 mM sulfo-N-hydroxysuccinimide (NHSS) in 167 mM MES at a pH of about 6.1 and 700 μL of 144 mM N-cyclohexyl-N'-(2-morpholinoethyl)carbodiimide metho-p-toluenesulfonate (CMC) in ethanol. We incubated with mixing (e.g., rotation) for about 30 minutes at room temperature. During this incubation time a NHSS ester is formed with the carboxylate groups of the polymer on the bead surface ("active ester"). We magnetically separated and discarded the supernatant. We washed once with about 1 mL of 50 mM 4-(2-hydroxyethyl)-1-piperazinepropanesulfonic acid (EPPS), at a pH of about 8.1. We added 634 μL deionized water, 200 μL of 250 mM EPPS of a pH of about 8.1 and 166 μL of a 1.51 mg/mL solution of β2GPI. We incubated with mixing (e.g., rotation) for about 60 minutes at room temperature. During this step the NHSS esters of the polymer on the bead surface are reacting with the amine groups of the β2GPI to form a peptide bond between the polymer of the bead surface and the protein. We washed the beads about 4 times with about 1 mL of 50 mM PBS/0.1% CHAPS to remove unbound β2GPI. We then stored the beads in 1 mL of 50 mM PBS/0.1% CHAPS at 2-8° C., a storage buffer, until needed.

We placed about 300 μL of succinylated cardiolipin (4.5 mg, 15 mg/mL in ethanol) into a 1.8 mL microfuge tube, to this solution we added about 9 μL of 334 mM N-hydroxysuccinimide (NHS) in ethanol and 19.5 μL of 168 mM CMC in ethanol. Samples were mixed gently for about 30 minutes at room temperature. During this incubation period a NHS ester is formed with the carboxylate group of the succinylated cardiolipin ("active ester"). Storage buffer was removed from β2GPI coated beads, which were then washed twice with about 1 mL of ethanol.

After reaction of the succinylated cardiolipin with NHS was completed, we transferred about 220 μL of that solution to the washed β2GPI coated beads and mixed for about one hour at room temperature. During this incubation period the NHS ester of the succinylated cardiolipin reacts with the amine groups of the β2GPI on the bead surface to form a peptide bond (i.e. covalent linkage). We washed the beads about 4 times with about 1 mL of a bead diluent comprising (0.5% gelatin; 6 mM sodium chloride; 50 mM 3-(N-Morpholino)propanesulfonic acid (MOPS); 0.1% 3-[(3-Cholamidopropyl)dimethylammonio]-1-propanesulfonate (CHAPS); 0.005% 2-(p-Methoxyphenoxy)propionic acid (PMP); 20% glycerol; 3.3 TIU/L aprotinin; and 2 mM magnesium chloride; pH 7.4). We then stored the beads in about 1 mL of bead diluent at about 2-8° C. until needed. A schematic representation of the preparation of the cardiolipin-β2GPI bead is shown in FIG. 3.

The cardiolipin-β2GPI protein bead was successfully used to detect anti-cardiolipin-cofactor protein antibodies from selected patient samples using the Luminex 100 platform. Table 1 shows the results of a comparison study between the assay of the present invention, BioPlex FCIA, and a commercially available enzyme immunoassay (EIA), demonstrating equivalence to the commercially available EIA.

TABLE 1

| BioPlex FCIA Cardiolipin/β2GPI Concordance Results versus Commercially Available EIA Kit | |
|---|---|
| Number of Samples in Study | 143 |
| Sensitivity | 96% |
| Specificity | 97% |
| Overall Agreement | 97% |

Example 2

Synthesis of Phosphatidylserine-β2GPI Beads

Into a 1.8 mL microfuge tube we placed about 10 mg of 8 μm carboxylate-modified paramagnetic microspheres. We washed once (using magnetic separation) with about 1 mL of 167 mM 2-(N-Morpholino)ethanesulfonic acid (MES), at a pH of about 6.1. We added about 300 μL of 668 mM sulfo-N-hydroxysuccinimide (NHSS) in 167 mM MES at a pH of about 6.1 and about 700 μL of 144 mM N-cyclohexyl-N'-(2- morpholinoethyl)carbodiimide metho-p-toluenesulfonate (CMC) in ethanol. We incubated the samples with mixing (e.g., rotation) for about 30 minutes at room temperature. We magnetically separated beads from the supernatant, which was discarded. Beads were washed once with about 1 mL of 50 mM 4-(2-hydroxyethyl)-1-piperazinepropanesulfonic acid (EPPS), at a pH of about 8.1. We added to the beads about 634 μL deionized water, about 200 μL of 250 mM EPPS pH 8.1 and about 166 μL of a 1.51 mg/mL solution of β2GPI and incubated with mixing (e.g., rotation) for about 60 minutes at room temperature. We washed the beads 4 times with about 1 mL of 10 mM PBS, at a pH of about 7.4. We then stored the beads in about 0.6 mL of 10 mM PBS, pH 7.4, storage buffer, at about 2-8° C. until needed.

We placed about 400 μL of 8.1 mg/mL phosphatidylserine in 10 mM PBS, pH7.4/1.5% CHAPS into a 1.8 mL microfuge tube, to create a solution. To this solution, we added about 12 μL of 334 mM sulfo-N-hydroxysuccinimide (NHSS) in 50 mM MES, pH 6.1 and about 26 μL of 168 mM CMC in ethanol. Samples were mixed gently for about 30 minutes at room temperature.

Figure 4:
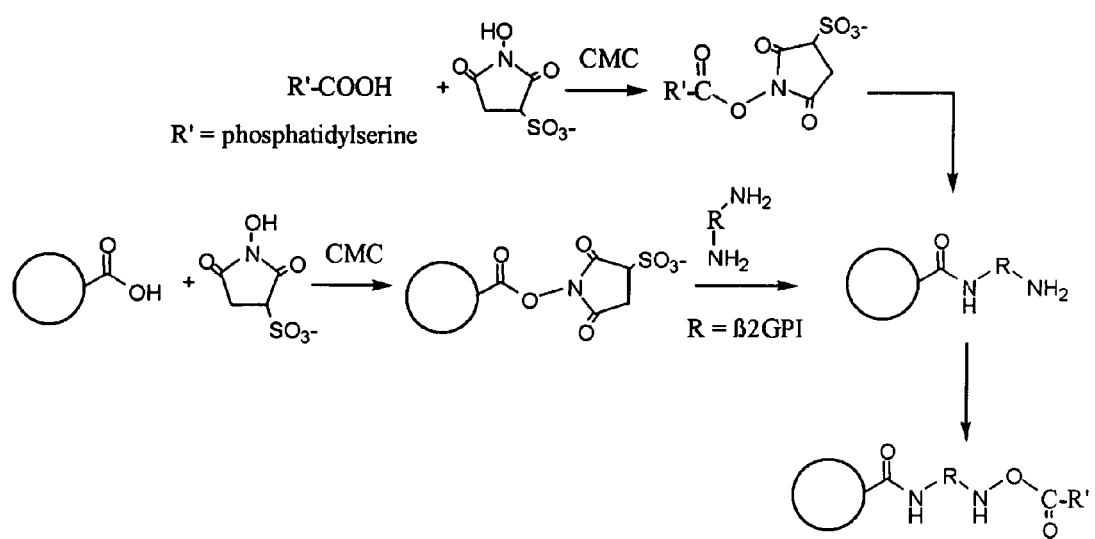
FIG. 4 provides a schematic for synthesis of a phosphatidylserine-β2GP microparticle. The microparticle is depicted as a large circle. CMC refers to N-cyclohexyl-N'-(2-morpholinoethyl)carbodiimide metho-p-toluenesulfonate. β2GPI refers to the beta-2-glycoprotein I (β2GPI) protein.

After the incubation of the solution was completed, we transferred about 359 μL of 10 mM PBS/1.5% CHAPS and 41 μL of the phosphatidylserine solution to the bead suspension. We incubated with mixing (e.g., rotation) for about 1 hour at room temperature. We washed the beads 6 times with about 1 mL of the bead diluent described above. We then stored the beads in about 1 mL of bead diluent at about 2-8° C. until needed. A schematic representation of the preparation of the phosphatidylserine-β2GPI bead is shown in FIG. 4. The results of a comparison study between the assay of the present invention using the phosphatidylserine-β2GPI beads and a commercially available enzyme immunoassay (EIA) are seen in Table 2, showing equivalence to the commercially available EIA.

TABLE 2

Phosphatidylserine/β2GPI Concordance Results versus Commercially Available EIA

| | |
|---|---|
| Number of Samples in Study | 188 |
| Sensitivity | 92% |
| Specificity | 99% |
| Overall Agreement | 96% |

Example 3

Diagnosis of APS Using Cardiolipin or Phosphatidylserine-β2GPI Beads

As seen in Table 3, blood samples were collected from ninety-seven healthy blood donors and 106 patients previously diagnosed with either primary or secondary Anti-Phospholipid Syndrome (APS). A panel of multiplexed differentiable particles coated (i.e., covalently attached) with 1) β2GPI only, 2) succinylated cardiolipin only, 3) succinylated cardiolipin and β2GPI and 4) phosphatidylserine and β2GPI was generated. For 3 and 4, both succinylated cardiolipin and phosphatidylserine were covalently bound to the β2GPI protein. Wahses were performed in buffers that included a detergent. The blood samples were assayed on the four differentiable particles by flow cytometry. No samples from the healthy donors exhibited binding to any of the four tested particles. In contrast, samples from sixty-one of the APS patients (58%) exhibited binding to at least one of the four particles. Conventional APS diagnostic tests detect antibodies that bind to β2GPI beads or β2GPI-cardiolipin beads. Seven of the APS patients below would not have been diagnosed using the conventional methods. Six exhibited binding to cardiolipin only beads and one exhibited binding to a phosphatidylserine only bead (not shown).

TABLE 3

Detection of antibodies in APS patients

| Bead | Number of APS Patients Identified by Test |
|---|---|
| Succinylated cardiolipin-β2GPI | 21 |
| β2GPI | 54 |
| Succinylated Cardiolipin | 18 |
| Phosphatidylserine-β2GPI | 49 |
| Prothrombin | 3 |
| Composite | 61 |
| Total Number of APS Patients | 106 |

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. An anti-phospholipid-cofactor protein-antibody detection reagent, the reagent comprising a phospholipid moiety, a beta-2-glycoprotein I (β2GPI) protein, and a carrier,
wherein the phospholipid moiety is covalently bound to the β2GPI protein via the polar head group of phospholipid and an amine group of the β2GPI protein and the β2GPI protein is bound to the carrier.

2. The detection reagent of claim 1, wherein the phospholipid moiety is a cardiolipin moiety, a phosphatidyserine moiety, a phosphatidylcholine moiety, a phosphatidylethanolamine moiety, a phosphatidylglycerol moiety, a phophatidylinositol moiety, or a phosphatidic acid moiety.

3. The detection reagent of claim 1, wherein the carrier is a microparticle or a microtiter plate.

4. The detection reagent of claim 1, wherein the β2GPI protein is covalently bound via another amine group to the carrier.

5. A method of detecting an anti-phospholipid-β2GPI protein-antibody in a biological sample, wherein the antibody specifically binds to an antigen selected from the group consisting of a phospholipid, β2GPI protein, and a phospholipid-β2GPI protein complex, the method comprising the steps of:
(a) contacting the biological sample with the detection reagent of claim 1; and
(b) detecting an antigen-antibody complex comprising the detection reagent of claim 1 and the anti-phospholipid-β2GPI protein-antibody, wherein detection of the antigen-antibody complex indicates the presence of the anti-phospholipid-β2GPI protein-antibody in the biological sample.

6. The method of claim 5, wherein the carrier is selected from a microparticle and a microtiter plate.

7. The method of claim 5, wherein step (b) is performed by flow cytometry.

8. The method of claim 5, wherein at least one step is performed in a buffer that comprises a detergent.

9. A method of diagnosing anti-phospholipid syndrome (APS) in a patient, the method comprising the steps of:

(a) contacting a biological sample from the patient with the detection reagent of claim 1; and (b) determining a level of an antigen-antibody complex comprising the detection reagent of claim 1 and an anti-phospholipid-β2GPI protein-antibody from the biological sample, wherein a difference in the level of the antigen-antibody complex in the biological sample from the patient and a biological sample from a normal control indicates that the patient has APS.

10. The method of claim 9, wherein the carrier is selected from a microparticle and a microtiter plate.

11. The method of claim 9, wherein the biological sample is blood or a blood product.

12. The method of claim 9, wherein step (c) is performed by flow cytometry.

13. The method of claim 9, wherein the phospholipid is selected from cardiolipin and phosphatidylserine.

14. A method of determining a likelihood of developing an anti-phospholipid syndrome (APS) in a patient, the method comprising the steps of:

a) determining in a sample from the patient a level of an antibody that binds to a cardiolipin-β2GPI protein complex comprising a cardiolipin moiety covalently bound to the β2GPI protein via the polar head group of the cardiolipin and an amine group of the β2GPI protein; and b) comparing the level of the antibody determined in step a) with level of the antibody from a normal control, wherein (i) the level of the antibody from the patient being less than or substantially equal to the level of the antibody from the normal control indicates low or no likelihood of developing APS; and (ii) the level of the antibody from the patient being higher than the level of the antibody from the normal control indicates an increased likelihood of developing APS.

15. The method of claim 14, further comprising the steps of: determining a level of an antibody that binds to a phosphatidylserine-β2GPI protein complex-comprising a phosphatidylserine moiety covalently bound to the β2GPI protein via the polar head group of the phosphatidylserine and an amine group of the β2GPI protein, and comparing the level to a level of the antibody from a normal control.

16. An anti-cardiolipin-cofactor protein-antibody detection reagent, the reagent comprising a cardiolipin moiety, a beta-2-glycoprotein I (β2GPI) protein, and a carrier, wherein the cardiolipin moiety is covalently bound to the β2GPI protein via the polar head of the cardiolipin and an amine group of the β2GPI protein and the β2GPI protein is bound to the carrier.

* * * * *